United States Patent [19]

Sanders et al.

[11] 4,007,137
[45] Feb. 8, 1977

[54] PROCESS FOR PRODUCING MIXTURE CONTAINING 4-(4-METHYL-4-HYDROXYAMYL)Δ³-CYCLOHEXENECARBOXALDEHYDE, PRODUCT PRODUCED, AND ITS PERFUME USES

[75] Inventors: James Milton Sanders, Eatontown; William L. Schreiber, Jackson; John B. Hall, Rumson, all of N.J.

[73] Assignee: International Flavors & Fragrances Inc., New York, N.Y.

[22] Filed: Oct. 7, 1975

[21] Appl. No.: 620,354

[52] U.S. Cl. .............................. 252/522; 260/598
[51] Int. Cl.² .................................. C11B 9/00
[58] Field of Search ............ 260/598, 488; 252/522

[56] References Cited

UNITED STATES PATENTS

| | | | |
|---|---|---|---|
| 2,842,598 | 7/1958 | Kitchens | 260/598 |
| 2,947,780 | 8/1960 | Teegarden et al. | 260/488 |
| 3,030,384 | 4/1962 | Somerville | 252/522 |
| 3,067,244 | 12/1962 | Robinson et al. | 260/598 |

OTHER PUBLICATIONS

E. F. Lutz et al. J. Amer. Chem. Soc. 86, 3899 1964.

*Primary Examiner*—Veronica O'Keefe
*Attorney, Agent, or Firm*—Arthur L. Liberman; Franklin D. Wolffe

[57] ABSTRACT

A process is described for reacting acrolein having the structure:

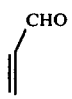

with myrcenol having the structure:

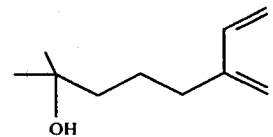

in the presence of a Lewis acid catalyst which is one of zinc chloride, zinc bromide or stannic chloride or mixtures thereof to produce a mixture containing a major proportion of 4-(4-methyl-4-hydroxyamyl)-Δ³-cyclohexenecarboxaldehyde which possesses a sweet, lilac-lily aromatic odor. The products produced by the aforementioned process are useful in various aspects of perfumery.

4 Claims, 5 Drawing Figures

EXAMPLE I

GLC PROFILE for REACTION PRODUCT RESULTING from ZnCl₂ - CATALYZED REACTION of MYRCENOL AND ACROLEIN

FIG. I
EXAMPLE I

GLC PROFILE for REACTION PRODUCT RESULTING from ZnCl₂-CATALYZED REACTION of MYRCENOL AND ACROLEIN

EXAMPLE VI

GLC PROFILE for REACTION PRODUCT RESULTING from NON-CATALYZED THERMAL REACTION of MYRCENOL and ACROLEIN INFRA RED SPECTRUM of PRODUCT of EXAMPLE III

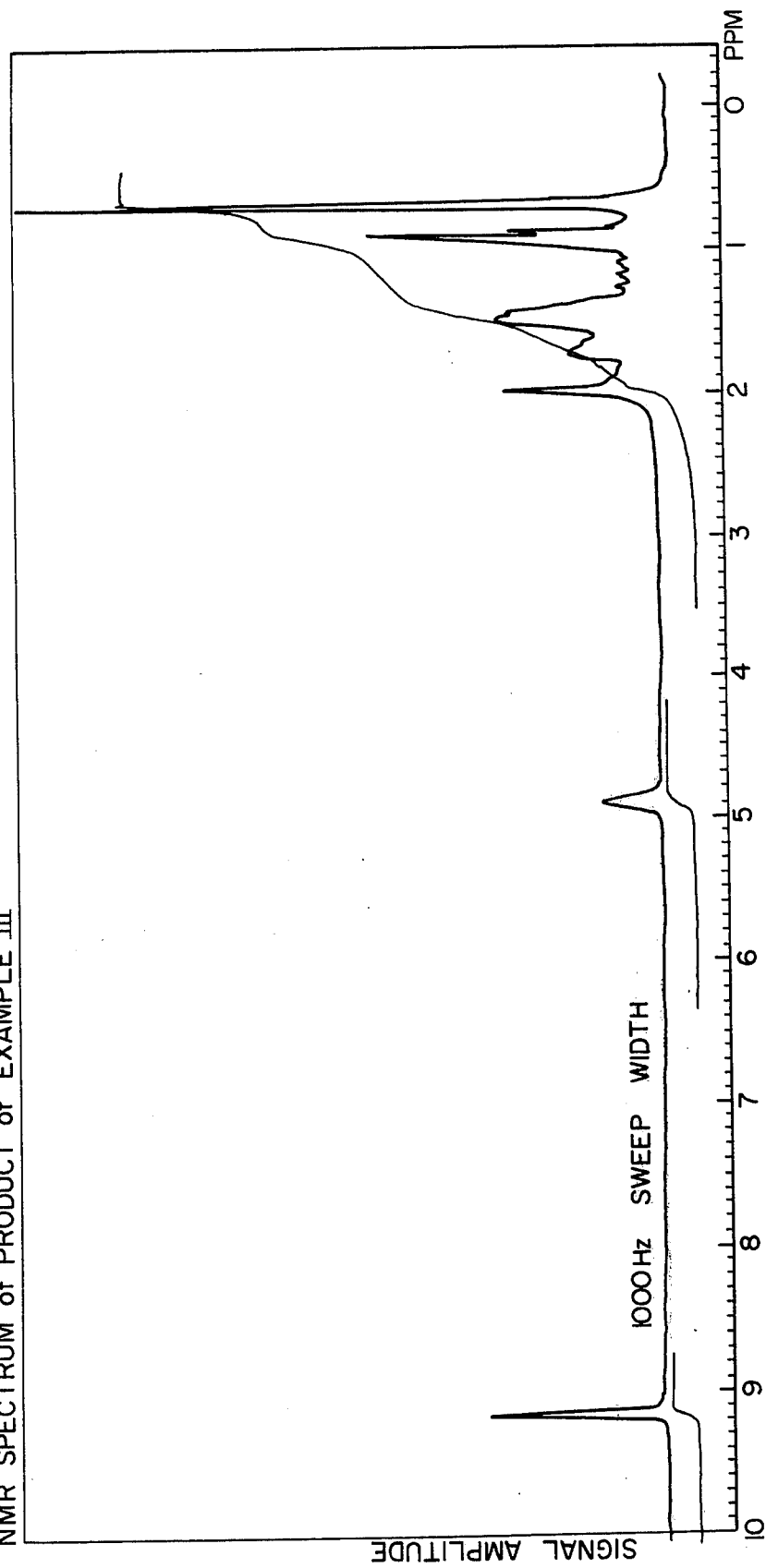

PROCESS FOR PRODUCING MIXTURE CONTAINING 4-(4-METHYL-4-HYDROXYAMYL)-Δ³-CYCLOHEXENECARBOXALDEHYDE, PRODUCT PRODUCED, AND ITS PERFUME USES

BACKGROUND OF THE INVENTION

The present invention relates to a process for producing 4-(4-methyl-4-hydroxyamyl)-Δ³-cyclohexenecarboxaldehyde in good yields and under relatively mild conditions; and the uses in perfumery of the products produced by such process.

The Diels-Alder reaction is well known in the field of organic chemistry, and the classic example thereof is the reaction of a conjugated diene with a conjugated alkylene carbonyl compound to provide a cyclic compound with unsaturation in the cyclic moiety. Since the original reaction was set forth, there have been many variations of the reaction. While certain compounds such as maleic anhydride and conjugated dienes react at room temperature to form cyclic derivatives, many other similar reactions require the use of more aggressive reaction conditions, and in many instances even these conditions do not provide very good yields of cyclic product.

4-(4-methyl-4-hydroxyamyl)-Δ³-cyclohexenecarboxaldehyde is indicated to be produced in U.S. Pat. No. 2,947,780, issued on Aug. 2, 1960, by means of reaction acrolein with myrcenol in a sealed reactor and heating the reaction mass to 150° C for a period of 4-½ hours accompanied by agitation. The reaction mass is then allowed to cool and the contents removed and subjected to fractional distillation. No mention of the use of a Lewis acid catalyst is set forth in U.S. Pat. No. 2,947,780.

U.S. Pat. No. 3,433,839 discloses a more complex process for preparing compounds having a structure similar to those prepared in the instant. U.S. Pat. No. 3,433,839 discloses a process for producing a mixture of alicyclic hydroxyaldehydes which comprises:

i. photo-oxidizing myrcene to produce a mixture of its hydroperoxides,
ii. reducing the resulting mixture to produce a mixture of 2-methyl-6-methylene-3,7-octadiene-2-ol and 2-methyl-6-methylene-1,7-octadiene-3-ol; and
iii. reacting the thus obtained mixture with a dienophile selected from the group consisting of acrolein and crotonaldehyde at 100° to 150° C for 3 to 6 hours to produce at least one mixture of alicyclic hydroxyaldehydes selected from the group consisting of where said dienophile is acrolein, 4-(4'-methyl-4'-hydroxy-2'-pentenyl)-3-cyclohexene-1-carboxaldehyde and 4-(4'-methyl-3'-hydroxy-4'-pentenyl)-3-cyclohexene-1-carboxaldehyde, and where said dienophile is crontonaldehyde, 4-(4'-methyl-4'-hydroxy-2'-pentenyl)-6-methyl-3-cyclohexene-1-carboxaldehyde and 4-(4'-methyl-3'-hydroxy-4'-pentenyl)-6-methyl-3-cyclohexene-1-carboxaldehyde.

The prior art is replete with disclosures of Diels-Alder reactions wherein Lewis acids are used as catalysts, as follows:

1. H. G. Oddy, *J. Amer. Chem. Soc.*, 45,2156 (1923). aluminum chloride catalyzed Diels-Alder reaction of anthracene and maleic anhydride.
2. A. N. Johnson, U.S. Pat. No. 2,724,730 (1955); CA, 51,7409b (1957). AlCl₃ catalyzed reaction of hexachlorocyclopentadiene with cyclopentene and hexachlorocyclopentene.
3. P. Yates and P. Eaton, *J. Amer. Chem. Soc.* 82,4436 (1960). AlCl₃ catalyzed reaction of anthracene and maleic anhydride.
4. G. I. Fray and R. Robinson, *J. Amer. Chem. Soc.*, 83,249 (1961); U.S. Pat. No. 3,067,244 (1962). Lewis acid catalyzed Diels-Alder reaction of butadiene, cyclopentadiene, or anthracene with various dienophiles (e.g., acrolein, methacrolein, acrylic aicd, methyl vinyl ketone). Only dienophiles having a terminal vinyl group are claimed.
5. H. M. Walborsky, L. Barash and T. C. Davis, *J. Org. Chem.*, 26,4778 (1961); *Tetrahedron*, 19,233 (1963). AlCl₃ catalyzed reaction of butadiene and (-)-dimenthyl fumarate.
6. I. A. Favorskaya and E. M. Auvinen, *Zh. Obshch. Khim.*, 33,2795 (1963); CA, 59,15191 d. BF₃ catalyzed reaction of isoprene or 2,3-dimethylbutadiene-1,3 with methyl vinyl ketone. 2-hexen-4-one, 1-propionylcyclopentene, and 1-propionylcyclohexene.
7. E. F. Lutz and G. M. Bailey, *J. Amer. Chem. Soc.*, 86,3899 (1964). Comparison of isomer ratio of thermal and SnCl₄ catalyzed reaction of isoprene with acrolein or methyl vinyl ketone.
8. a. T. Inukai and M. Kasai, *J. Org. Chem.*, 30,3567 (1965). b. T. Inukai and T. Kojima, *J. Org. Chem.*, 31,1121 (1966). Lewis acid catalyzed reaction of isoprene with various acrylic acid derivatives.
9. British Pat. No. 1,076,304 (1965); CA, 68,49177 f (1968). AlCl₃ catalyzed reaction of methyl acrylate, methyl methacrylate, or acrylonitrile with isoprene, piperylene, chloroprene, cyclopentadine, or 1,3-butandiene. (cf. U.S. Pat. No. 3,390,169).
10. G. P. Kugatova-Shemyakina, L. I. Rozhkova, V. N. Gramenitskaya and V. M. Andreev. *J. Org. Chem. USSR*, 62,459 (1970). Catalysis of the reaction of acrolein or crotonaldehyde with isoprene or piperylene.
11. S. R. Wallis. *J. Amer. Chem. Soc.*, 92,3218 (1970). AlCl₃ catalyzed Diels-Alder reaction of butadiene with 2-phenyl-2-cyclohexenone.
12. French Pat. No. 2,149,051, D. De Ryke and H. Boelens. ZnCl₂ catalysis of Diels-Alder reaction of 2-hexenal with 2-methyl-1,3-pentadiene and with cyclopentadiene.

In addition, Lewis acid catalyzed Diels-Alder reactions wherein the dienophile is alpha,beta-disubstituted with alkyl groups are disclosed in U.S. Pat. No. 3,852,358, issued on Dec. 3, 1974.

British Pat. No. 1,383,942, published on Feb. 12, 1975 disclosed processes for producing 6-propyl-3-cyclohexene carboxalhydes of the general formula:

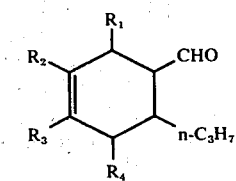

and processes for producing same wherein an alkadiene of the general formula:

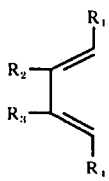

undergoes a Diels-Alder reaction with 2-hexene-1-al. In Example I, of British Pat. No. 1,383,942, 2-methyl-1,3-pentadiene is shown to be reacted with 2-hexene-1-al in the presence of a zinc chloride catalyst at reflux temperature, 75° C. However, the reaction mass is maintained at 120° C for 1 hour and it is indicated that this reaction must maintained at the higher temperature for that period of time.

German Offenlegungschrift No. 2,403,631, published on Aug. 8, 1974, discloses a process for producing such compounds as 3-methyl-5-(3-methyl-3-hydroxy-butyl)-3-cyclohexenecarboxaldehyde the last step of which is a thermal, non-catalytic Diels-Alder reaction:

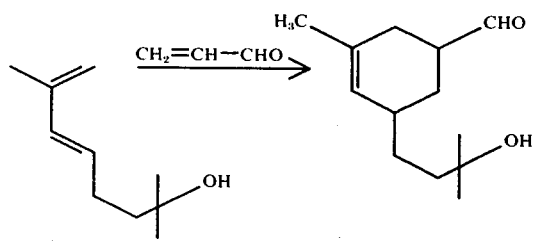

U.S. Pat. No. 2,373,568 shows the Diels-Alder reaction of methacrolein and cyclopentadiene under pressure at about 140° C to provide a material with a camphoraceous aroma and the further reaction of the Diels-Alder product with acetone and sodium methylate to provide a product with a floral type odor. Vaughan et al. in J.A.C.S. 74,5355show the reaction of mesityl oxide and cyclopentadiene produced in situ by thermal depolymerization of the dimer to provide an unsaturated ketone by carrying out the reaction at 160° C for 12 hours to provide a 21 percent yield, based upon cyclopentadiene, although the yield based upon mesityl oxide consumed was said to be 60 percent.

Chemical Abstracts 47, 12271e shows a diene condensation at 160° C in the presence of pyrogallol. A condensation of isoprene and other materials with mesityl oxide at 200° C is shown in Chemical Abstracts 72, 8985p. The use of haloacetic acids as catalysts in diene reactions is shown in French Patent No. 838,454. Wasserman concluded that diene synthesis rates were not appreciably affected by a number of catalysts including ferric chloride in ethanol in J. Chem. Soc. 3346 (1949).

Chemical Reviews 31, 441 reported a reaction between anthracene, maleic anhydride and aluminum chloride. U.S. Pat. No. 2,724,730 shows the condensation of hexachlorocylopentadiene with a dienophilic compound in the presence of alumiumn chloride at 100° C. Aluminum Chloride is said to catalyze a Diels-Alder reaction in J. Org. Chem. 26, 4778. The International Edition of Angew. Chem. 6, 24 states that Lewis-acids have an effect on the yields of stereoisomers in diene additions and mentions the possibility of an investigation of reaction at low temperature in the presence of Lewis-acids under mild conditions to obtain uniform Diels-Alder Products. A low temerature Diels-Alder reaction is shown in Chemical Abstracts 59, 15191d, and regulation of structural isomerism and acceleration of Diels-Alder reaction is shown in J.A.C.S. 86, 3899. Diels-Alder reactions catalyzed by aluminum chloride are also shown in J. Organic. Chem. 32, 1121. See also Tetrahedron 19, 2333 (1963).

The Diels-Alder reaction of certain aldehydes with dienes in the presence of stannic chloride and boron trifluoride is shown in a translation of an article from Zh. Org. Chimii 6, 2446. Dienophilic compounds for Diels-Alder reactions are shown in Chemical Review 31, 327 and in Onishchenko, Diene Synthesis at page 904ff. British Patent No. 835,840 (also J.A.C.S. 82,4436) shows acceleration of the Diels-Alder reaction with stannic chloride. Acceleration with aluminum chloride is shown in J.A.C.S. 82,4436. U.S. Pat. Nos. 3,047,433 and 3,067,244 show the use or production of Diels-Alder adducts.

British Patent Specification No. 1,076,304 shows a Diels-Alder reaction to produce nitriles and esters. Thus, nothing in the prior art is considered to teach explicitly or implicitly a low temperature reaction to produce mixtures containing a high proportion of 4-(4-methyl-4-hydroxyamyl)-Δ³-cyclohexenecarboxaldehyde.

BRIEF DESCRIPTION OF THE DRAWINGS

FIG. 5 is the NMR spectrum of the product of Example III.

THE INVENTION

Figure 1:
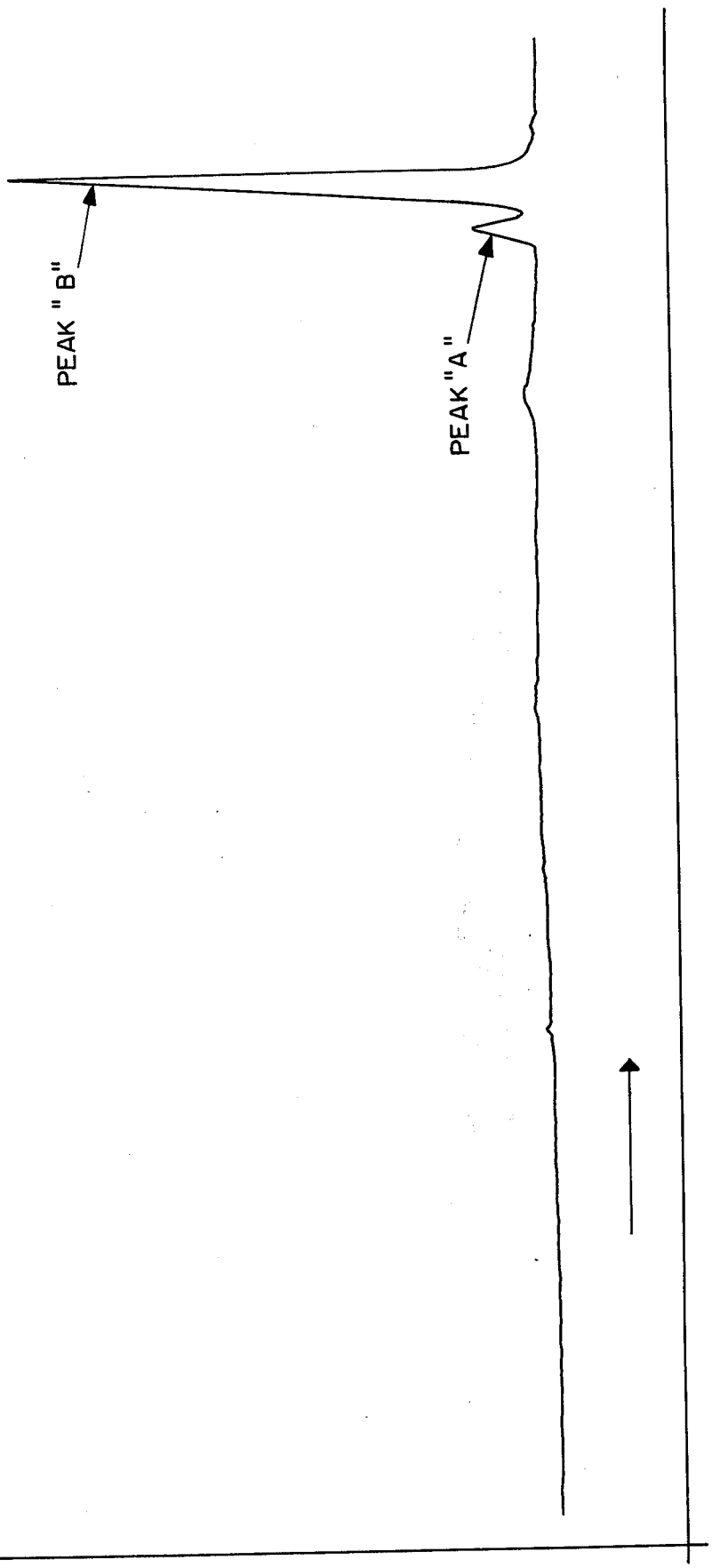
FIG. 1 is the GLC (gas-liquid chromatagraphy) profile for the reaction product resulting from the zinc chloride catalyzed reaction of myrcenol and acrolein exemplified in Example I.

Surprisingly, it has been found that myrcenol, having the structure:

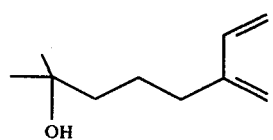

can be reacted with acrolein, having the structure:

under mild conditions in the presence of at least one of the specific catalysts, zinc chloride, zinc bromide and stannic chloride to obtain the Diels-Alder reaction product, 4-(4-methyl-4-hydroxyamyl)-Δ³-cyclohexenecarboxaldehyde, in good yields and in relatively short times.

Briefly, the present invention contemplates, interalia, a process to provide mixtures containing a major proportion of 4-(4-methyl-4-hydroxyamyl)-Δ³-cyclohexenecarboxaldehyde which process comprises steps of intimately admixing acrolein with myrcenol:

1. In the presence of a catalytic quantity of a Lewis acid catalyst selected from the group consisting of:
   zinc chloride;
   stannic chloride;
   zinc bromide;
   or a mixture of two or more of said Lewis acids;
2. At a temperature in the range of from about 0° C up to about 100° C; and
3. At a pressure of from about 1 atmosphere to about 100 atmospheres.

Depending on the specific catalyst used, the resulting product which is a mixture of compounds having the structures:

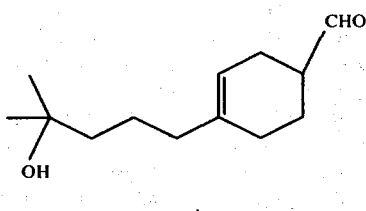

and

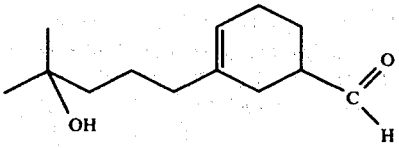

is produced in various isomer ratios. From an aroma and perfumery standpoint it is highly desirable to produce a mixture containing as much as possible of the 4-(4-methyl-4-hydroxyamyl)-Δ³-cyclohexenecarboxaldehyde having the structure:

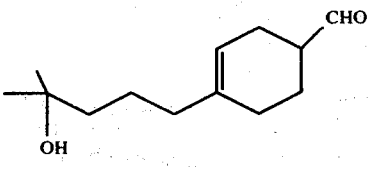

The following tables set forth the isomer ratios of the compound having the structure:

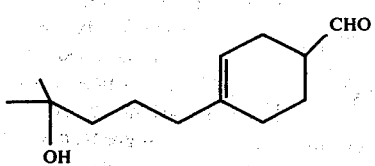

to the compound having the structure:

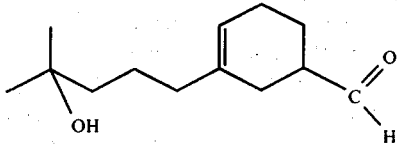

produced by both the "thermal" method of the prior art (U.S. Pat. No. 2,947,780) and the catalytic method of the instant invention:

TABLE I

| NATURE OF REACTION | RATIO OF COMPOUND HAVING THE STRUCTURE ![CHO structure with OH] TO COMPOUND HAVING THE STRUCTURE ![aldehyde structure with OH] |
|---|---|
| Thermal reaction of U.S. Patent No. 2,947,780 (Example V, infra) | 2.5:1 |
| Zinc chloride catalyzed reaction of Examples I-III, infra | 9:1 |
| Stannic chloride catalyzed reaction of Example IV, infra | 38:1 |

The mole ratio of acrolein reactant:myrcenol reactant is required to be in the range of from about 10:1 to about 1:10 with the most preferable mole ratio being about 1:1.

The temperature of reaction varies from −20° C up to 100° C but the preferable temperature range is a function of the particular catalyst used. Thus, when using a zinc chloride or a zinc bromide catalyst, the temperature of reaction can vary between 20° and 80° C, with a temperature range of 40°–50° C being the most desired range. When using stannic chloride, the temperature range usable if −20° C up to 50° C with the most preferred temperature range being 0°–10° C.

One of the outstanding advantages of the present process is the fact that only modest temperatures are required to achieve good yields and satisfactory reaction times. Even at the above-mentioned modest temperatures, reaction times of the order of from about 1 up to 10 hours are achieved, and it is generally preferred to carry out the reaction for about from 7 to 9 hours.

The quantity of catalyst varies from about 0.2% up to about 10% (of the reaction mass) and is related to the temperature and time of reaction. The most preferred amount of catalyst (percent based on total weight of reactant used) is from 1 up to 2%.

The reaction of our invention can be carried out over a range of pressures, but since the process does not require special high-pressure techniques like those of the prior art, it is especially preferred to conduct the reaction at atmospheric pressure.

Another of the advantages of the present invention is the freedom in admixing reagents. It is possible to use any combination of sequential or simultaneous addition of the myrcenol, acrolein and catalyst. It has been found desirable in obtaining the highest possible yields to first admix the catalyst with the myrcenol. Then, with good agitation the acrolein is added, for example using a metering pump, over a period of time of from 3 to about 6 hours, while maintaining the reaction temperature in the desired temperature range.

The resulting product from the process of our invention can be washed with salt solutions, such as sodium chloride solutions, to facilitate separation of reaction products from catalyst and to provide an initial cleansing of the product. The reaction product is recovered from the reaction mixture and can then be subjected to conventional purification and/or isolation techniques such as distillation, extraction, preparative chromatographic tenchinques and the like. It is especially preferred to purify the materials by vacuum distillation, and adjuvant materials such as anti-oxidants, petroleum base oils, trialkanolamines and the like can be used. Triethanolamine and calcium carbonate are preferred agents for scavenging traces of acids before or during the distillation.

It is also possible, but not necessarily desirable, to carry out the reaction in the presence of a liquid reaction vehicle. If such a vehicle is used, it is preferably a solvent for the reactants and product of reaction. Such solvent is to be inert under the reaction conditions. Preferred reaction vehicles include methylene discloride, toluene, benzene, diethylether, other ethers esters, nitriles, nitro compounds and chlorinated solvents, particularly halogenated mononuclear aromatic hydrocarbons, such as dichlorobenzene, and the like. The quantity of vehicle utilized can range from none to about 300 g for each mole of myrcenol in the reaction mixture. It is preferred to use up to 250 g of vehicle for each mole of the myrcenol.

In summary, the advantages of the instant process for preparing reaction products containing major quantities of 4-(4-methyl-4-hydroxyamyl)-$\Delta^3$-cyclohexenecarboxaldehyde are as follows:
1. The reaction can be carried out in standard vessels without pressure equipment or continuous flow equipment.
2. The reaction can be carried out at moderate temperatures.
3. The reaction gives rise to high-throughput, high conversion, and high yield.
4. The noxious odor as well as the toxicity of acrolein can be easily contained by using the procedures of the instant invention.
5. The isomer ratio of the product having the structure:

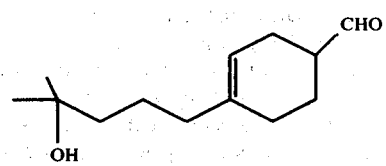

to the product having the structure:

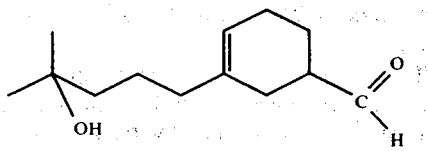

is in favor of the compound having the structure:

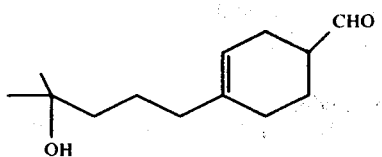

relative to the thermal Diels-Alder reaction used to produce reaction products containing high proportions of 4-(4-methyl-4-hydroxyamyl)-$\Delta^3$-cyclohexenecarboxyaldehyde.

The mixture containing 4-(4-methyl-4-hydroxyamyl)-$\Delta^3$-cyclohexenecarboxaldehyde produced according to the process of our invention and one or more auxiliary perfume ingredients, including for example, alcohols, other aldehydes, nitriles, esters, cyclic esters, and natural essentiaL oils, may be admixed so that the combined odors of the individual components produce a pleasant and desired fragrance, particularly and preferably in lilac, floral, fougere, bouquet and rose fragrances. Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation; and (d) topnotes which are usually low boiling fresh smelling materials.

In perfume compositions, it is the individual components which contribute to their particular olfactory characteristics, however, the over-all sensory effect of the perfume composition will be at least the sum total of the effects of each of the ingredients. Thus, the mixture containing 4-(4-methyl-4-hydroxyamyl)-$\Delta^3$-cyclohexenecarboxaldehyde produced according to the process of our invention can be used to alter, modify or enhance the aroma characteristics of a perfume composition, for example, by utilizing or moderating the olfactory reaction contributed by another ingredient in the composition.

The amount of mixture containing 4-(4-methyl-4-hydroxyamyl)-$\Delta^3$-cyclohexenecarboxaldehyde produced according to the process of our invention, which will be effective in perfume compositions as well as in perfumed articles and colognes depends on many factors, including the other ingredients, their amounts, and the effects which are desired. It has been found that perfume compositions containing as little as 0.01% of the mixture containing 4-(4-methyl-4-hydroxyamyl)-$\Delta^3$-cyclohexenecarboxaldehyde produced according to the process of our invention, or even less (e.g., 0.005%) can be used to impart (or augment, enhance or modify) a sweet, lilac-lily aromatic odor to (or in) soaps, cosmetics or other products. The amount employed can range up to 70% of the fragrance components and will depend on considerations of cost, nature of the end product, the effect desired on the finished product, and the particular fragrance sought.

The mixture containing 4-(4-methyl-4-hydroxyamyl)-$\Delta^3$-cyclohexenecarboxaldehyde produced according to the process of our invention is useful, taken alone or in perfume compositions, or as an olfactory component in detergents and soaps, space odorants and deodorants, perfumes, colognes, toilet water, bath preparations such as bath oils and bath solids, hair preparations (such as lacquers, brilliantines, pomades and shampoos), cosmetic preparations (such as creams, deodorants, hand lotions and sun screens), & powders (such as talcs, dusting powders, face powders and the like). When used as an olfactory component, as little as 1% of the mixture containing 4-(4-methyl-4-hydroxyamyl)-$\Delta^3$-cyclohexenecarboxaldehyde produced according to the process of our invention will suffice to impart a pleasant lilac-lily note to lilac, floral, fougere, bouquet, and rose formulations. Generally, no more than 8% of the mixture containing 4-(4-methyl-4-hydroxyamyl)-$\Delta^3$-cyclohexenecarboxaldehyde produced according to the process of our invention, based on the ultimate end product, is required in the perfume composition.

In addition, the perfume composition or fragrance composition of our invention can contain a vehicle, or carrier for the mixture containing 4-(4-methyl-4-hydroxyamyl)-$\Delta^3$-cyclohexenecarboxaldehyde produced according to the process of our invention. The vehicle can be a liquid such as a non-toxic alcohol, a non-toxic glycol, or the like. The carrier can also be an absorbent solid, such as a gum (e.g. gum arabic) or component for encapsulating the composition (such as gelatin).

The following Examples I–XV are given to illustrate embodiments of the invention as it is presently preferred to practice it. It will be understood that these examples are illustrative and the invention is not to be considered as restricted thereto except as indicated in the appended claims.

The following Example VI illustrates the thermal Diels-Alder reaction of the prior art (U.S. Pat. No. 2,947,780).

The following Examples VII–XV illustrate the utility of the product produced by the process of the instant invention in perfumery.

All parts and percentages are by weight unless otherwise indicated.

EXAMPLES I, II and III

Into a 12-liter reaction flask equipped with mechnical stirrer, thermometer, metering pump, reflux condenser and heating mantle is placed 6600g (42.8 moles) of myrcenol and 90g (0.66 moles) of zinc chloride.

The resulting mixture is then heated to 45° C, and the heating mantle is removed. With good agitation, 2400g (42.8 moles) of acrolein is added via the metering pump over a 5–6 hour period with the reaction temperature maintained at 45°–50° C using a cooling bath.

After the exothermic reaction has subsided, the heating mantle is replaced, and the reaction mass is maintained at a temperature of 45°–50° C for two hours. The reaction mass is then transferred to a separatory funnel and washed at 60° C with 4500 ml of 10% aqueous sodium chloride solution and then with 4500 ml 10% aqueous sodium carbonate.

By carrying out the foregoing procedure, a yield of 8928 g of crude product is obtained. Analysis of this material by internal standard gas-liquid chromatography indicates 88.8% of 4-(4-methyl-4-hydroxy-amyl)-$\Delta^3$-cyclohexencarboxaldehyde and, by area normalization, 9.2% myrcenol. This represents an 87.5% conversion and essentially 100% chemical yield of 4-(4-methyl-4-hydroxyamyl)-$\Delta^3$-cyclohexenecarboxaldehyde based on myrcenol.

Two additional experiments are carried out using concentrations of zinc chloride different from that used in Experiment I. Summaries of these two experiments, as well as Experiment I, are set forth in the following Table II.

TABLE II

| | Reactants | | | | Analysis of Washed Crude | | | |
| Experiment | Myrcenol wt (moles) | Acrolein wt (moles) | ZnCl$_2$ wt (wt%)$^a$ | wt. | 4-(4-methyl-4-hydroxyamyl)-$\Delta^3$-cyclohexene-carboxaldehyde (wt) | % Myrcenol (wt) | % Conversion | % Yield |
|---|---|---|---|---|---|---|---|---|
| I | 6600 g (42.8) | 2400 g (42.8) | 88 g (1%) | 8928 g (7928 g) | 88.8 | 9.2 (821 g) | 87.5 | 100 (estimate) |
| II | 2633 g (17.1) | 912 g (16.3) | 50 g (1.4%) | 3653 g (3138 g) | 85.9 | 10.5 (384 g) | 85.4 | 100 (estimate) |
| III | 2002 g (13) | 728 g (13) | 54.6 (2%) | 2847 g (2366 g) | 83.1 | 9.2 (262 g) | 86.9 | 100 (estimate) | a: Based on total reactants

The GLC profile (conditions: 500 × 0.03 carbowax 20M coated stainless steel open tubular column programed from 80° to 180° C at 2° C per minute) for the reaction product of Example I is shown in FIG. 1. The major peaks are A (9.3%) and B (90.3%).

Figure 4:
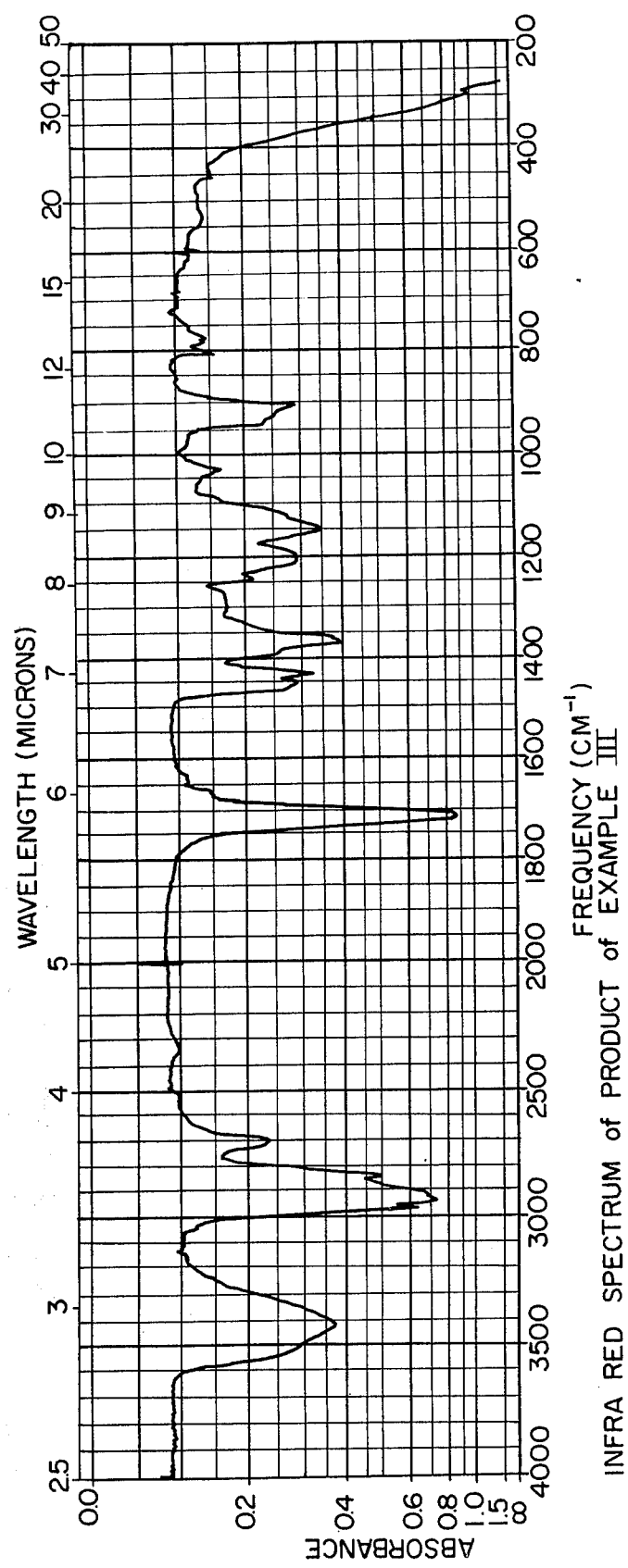
FIG. 4 is the infra red spectrum of the product of Example III.

The infra-red spectrum of the reaction product is set forth in FIG. 4. The NMR spectrum of the reaction product is set forth in FIG. 5.

Infr-Red Analysis 905, 1145, 1200, 1305, 1320, 1430, 1445, 1715, 2830, 2900, 2930, 2960, 3430cm$^{-1}$

| NMR Analysis, 100 MHz (Solvent: CDCl$_3$) | | |
|---|---|---|
| Peak | Interpretation | |
| 1.16 ppm (s) | $\begin{array}{c}CH_3\\ \diagdown\\ CH_3 \diagup\end{array}\!\!C\!-\!O-$ | 6 H |
| 1.42 (m) | $-CH_2-$ | 4 H |
| 2.32 – 1.67 (m) | $=C-CH_2-$ $+CH_2-C-O-$ | 8 H |
| 2.50 (m) | $OH- + HC-C=O$ | 2 H |

-continued

NMR Analysis, 100 MHz (Solvent: CDCl₃)

| Peak | Interpretation | |
|---|---|---|
| 5.42 (m) | $-\underset{\mid}{C}=\underset{\mid}{\overset{H}{C}}-$ | 1 H |
| 9.65 (s) | HC=O | 1 H |

EXAMPLE IV

Into a 2-liter reaction flask equipped with mechnical stirrer, thermometer, addition funnel, and reflux condenser is added, with stirring 5.2 g of SnCl₄ and 300 g of toluene. The resulting mixture is cooled to 3° C. With good agitation, 168 g (3 moles) of acrolein dissolved in 100 g of toluene is added over a five-minute period with the reaction temperature being maintained at 3° C. Over a period of four hours, 320 g (2 moles myrcenol is charged to the reaction flask with stirring while maintaining the temperature mass in the range of 2° C–5° C.

200 g of ice is added to the reaction mass together with 300 g of water, the mixture is stirred for a period of 15 minutes, and the phases are separated. The aqueous phase is the extracted with one 100 cc portion of toluene, and the organic layers are combined and washed with two 100 cc portions of saturated sodium chloride solution. One gram of Ionol and 10 g of triethanolamine are added to the washed organic solution which is distilled rapidly through a short column without fractionation.

The distillate collected at 141°–153° C and 1.4–3.0 mm Hg is then fractionated using a 12 × 1 Goodloe packed column to give 276 g of product (B.P. 125°–126° C/0.7 mm Hg).

Figure 2:
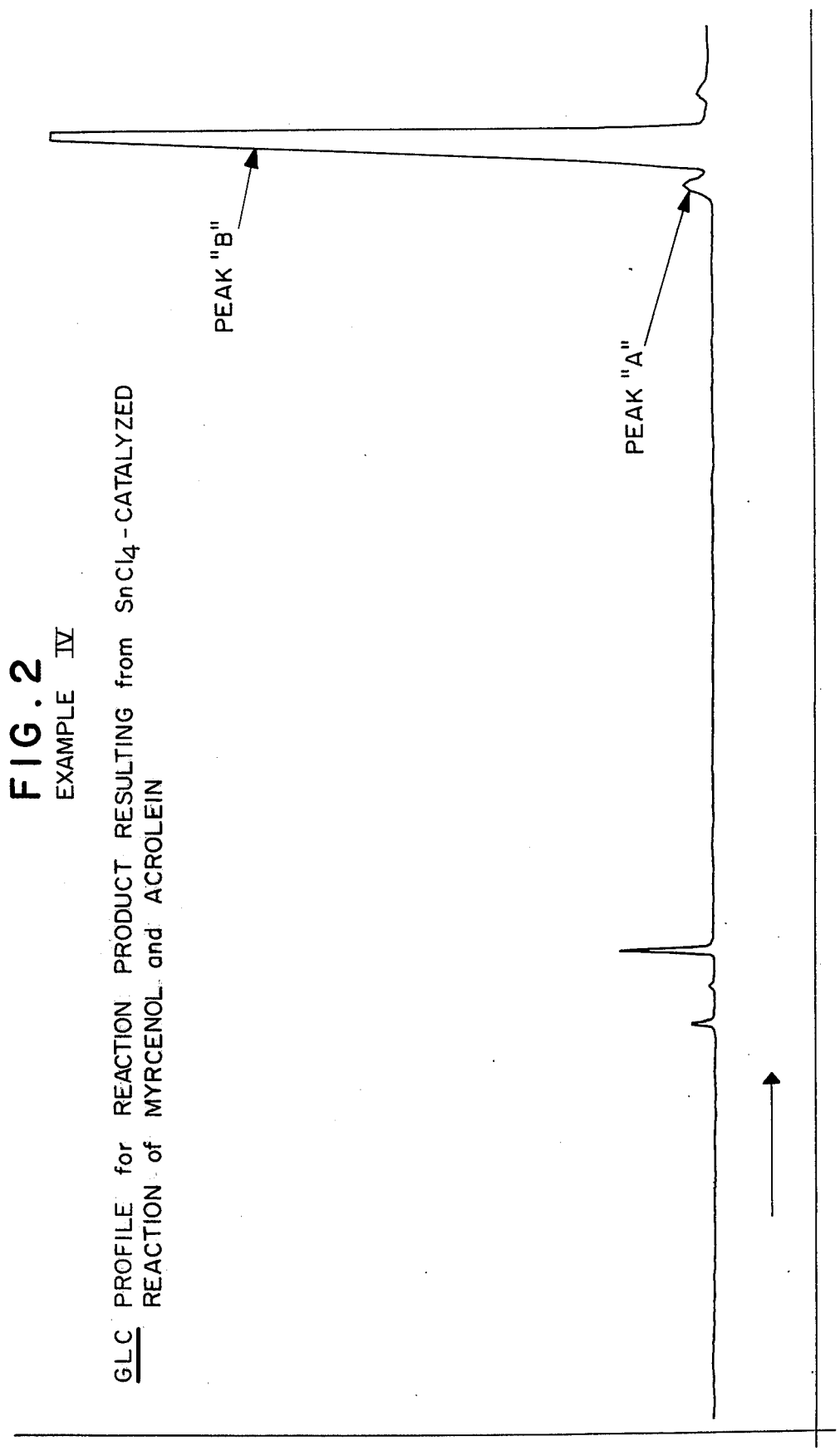
FIG. 2 is the GLC profile for the reaction product resulting from zinc chloride catalyzed reaction of myrcenol and acrolein exemplified in Example IV.

The GLC profile (conditions as in Example I) for the reaction product resulting from the SnCl₄ catalyzed reaction of myrcenol and acrolein is set forth in FIG. 2, the peaks being A (2.5%) and B (93.8%).

EXAMPLE V

A 22-liter reaction flask equipped with a thermometer, air driven stirrer, two addition funnels, reflux condenser, and cooling bath is charged with 2500 g toluene and 32.5 g of anhydrous stannic chloride. One of the addition funnels is charged with 3850 g (25.0 moles) of myrcenol, and the other additional funnel is charged with a solution of 1540g (27.5 moles) of acrolein in 2500 g of toluene. The flask contents are stirred and cooled to 0° C. Approximately 10% of the acrolein solution is added and the contents of both separatory funnels are then added simultaneously at approximately equal rates over a five hour interval. After about 40% of the addition, GLC analysis indicated that the reaction was slow, and therefore an additional 32.5 g of catalyst was added. The reaction temperature is maintained at 0°–5° C for most of the addition of reactants and for 1 hour after the addition. The reaction mass is then maintained at 4°–12 ° C for 45 minutes. A solution of 50 g of sodium hydroxide in 1-liter of water followed by 5 Ionox are then added with good agitation. The mixture is then allowed to settle. The aqueous phase is then extracted with 1200 g of toluene and the organic layers are combined and are washed twice with one liter portions of saturated sodium chloride solution.

Triethanolamine (75 g) is added, and the resulting material is distilled without fractionation. The distillate collected at a vapor temperature of 155°–163° C and a pressure of 0.8–1.1 mm Hg is then fractionally distilled using a 12 × 1 Goodloe packed column to give 3000 g of product, b.p. 133°–135° C at 0.5 –0.9 mm Hg.

EXAMPLE VI 575 grams myrcenol, 432 grams acrolein, and 10 grams hydroquinone are combined in a sealed reactor and heated to 150° C for 4 ½ hours accompanied by agitation. The reactor is allowed to cool, and the contents are removed and subjected to vacuum fractionation. After a forerun of unreacted inert isomeric C₁₀ alcohols distills off, there are obtained 640 g of product of B.P. 126°–135° at 2 mm Hg. On redistillation, there is obtained 442 g of product of B.P. 120°–122° C at 1 mm Hg, with a refractive index of 20° C, 1.4915; specific gravity at 20° C, 0.9941; ultraviolet absorption maximum, 292 millimicrons. The product tests 99.7% aldehyde by oximation test. Yield by weight = 56.8%, based on the myrcenol used. The product is 4-(4-methyl-4-hydroxyamyl)-Δ³-cyclohexenacarboxaldehyde.

This product has a very sweet lilac-lily aromatic odor.

Figure 3:
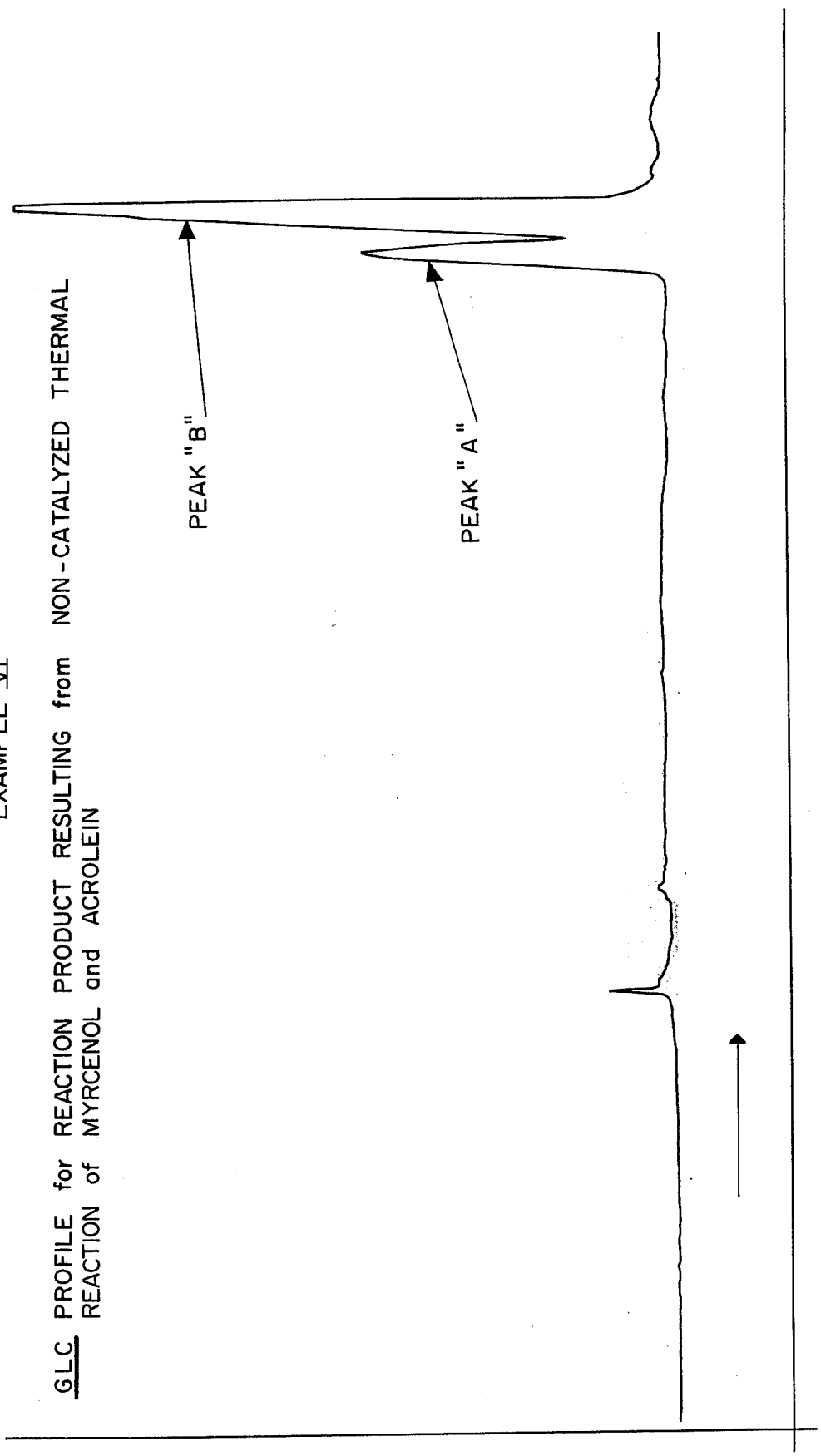
FIG. 3 is the GLC profile for the reaction product resulting from the non-catalyzed thermal Diels-Alder reaction of myrcenol and acrolein exemplified in Example VI.

The GLC profile (conditions as in Example I) for the reaction product resulting from the thermal non-catalyzed reaction of myrcenol and acrolein is set forth in FIG. 3 and indicates two major peaks, A (27.8%) and B (69.7%).

EXAMPLE VII

A perfume composition of the "Fougere" type is produced:

| Part by weight | Ingredients |
|---|---|
| 50 | cinnamic alcohol |
| 40 | musk ambrette |
| 5 | vanillin |
| 80 | coumarin |
| 10 | oakmoss resinoid |
| 125 | linalool |
| 150 | linalyl acetate |
| 50 | benzyl acetate |
| 70 | phenylethanol |
| 100 | oil of bergamot |
| 150 | oil of lavender 45/47 |
| 50 | geranium oil (Bourbon) |
| 50 | sandlewood oil E.I. |
| 5 | eugenol |
| 15 | isoeugenol |
| 20 | amyl salicylate |
| 20 | benzyl salicylate |
| 20 | product produced according to Ex. I containing major proportion of 4-(4-methyl-4-hydroxyamyl)-Δ³-cyclohexenecarboxaldehyde |
| 1010 | |

This product produced by Example I imparts a very sweet lilac-lily aromatic odor to this "Fougere" formulation.

EXAMPLE VIII

A perfume composition of the "Rose" type is produced by admixing the following ingredients:

| Parts by Weight | Ingredients |
|---|---|
| 20 | phenylethyl phenyl acetate |
| 40 | phenylethyl salicylate |

-continued

| Parts by Weight | Ingredients |
|---|---|
| 150 | geraniol |
| 240 | phenylethanol |
| 150 | citronellol |
| 20 | sandlewood oil E.I. |
| 75 | nonane diacetate - 1,3 |
| 50 | geranyl acetate |
| 20 | geranyl phenylacetate |
| 20 | citronellyl formiate |
| 25 | phenylethyl acetate |
| 60 | phenylethyl propionate |
| 20 | phenylacetaldehyde 50% in diethylphthalate |
| 20 | phenylacetaldehyde 1,3 - butyleneglycolacetal |
| 10 | eugenol |
| 10 | methylisoeugenol |
| 50 | alpha-hexylcinnamic aldehyde |
| 40 | product produced by the process of Ex. III containing a major proportion of 4-(4-methyl-4-hydroxyamyl)-Δ³-cyclohexenecarboxaldehyde |
| 1030 | |

This "Rose" perfume has a sweet floral aroma enhanced by addition thereto of the product produced according to Example III.

EXAMPLE IX

A perfume composition of the "Bouquet" type is produced by admixing the following ingredients:

| Parts by Weight | Ingredients |
|---|---|
| 20 | musk ambrette |
| 40 | heliotropine |
| 100 | benzyl acetate |
| 80 | 4-tert.butyl cyclohexyl acetate |
| 130 | alpha-hexylcinnamic aldehyde |
| 40 | alpha-amylcinnamic aldehyde |
| 30 | linalyl acetate |
| 80 | terpineol |
| 80 | geranyl acetate |
| 80 | linalool |
| 100 | alpha-methyl jonone |
| 25 | methyl isoeugenol |
| 15 | isoeugenol |
| 40 | geraniol |
| 60 | phenylethanol |
| 20 | styrallyl acetate |
| 50 | vetiveryl acetate |
| 5 | 10-undecene-1-al |
| 5 | product produced according to Example IV containing a major porportion of 4-(4-methyl-4-hydroxyamyl)-Δ³-cyclohexenecarboxaldehyde |
| 10000 | |

Addition of the product produced according to Example IV imparts a sweet lilac-lily nuance to this "Bouquet" type perfume composition.

EXAMPLE X

PREPARATION OF A COSEMTIC POWDER-COMPOSITION

A cosmetic powder is prepared by mixing in a ball mill, 100 g of talcum powder with 0.25 g of the mixture containing 4-(4-methyl-4-hydroxyamyl)-Δ³-cyclohexenecarboxaldehyde prepared according to Example I. It has an excellent sweet, lilac-lily aroma.

EXAMPLE XI

PERFUMED LIQUID DETERGENT

Concentrated liquid detergents with a sweet, lilac-lily odor prepared containing 0.10%, 0.15% and 0.20% of the mixture containing 4-(4-methyl-4-hydroxyamyl)-Δ³-cyclohexenecarboxaldehyde prepared according to Example VI. They are prepared by adding and homogeneously mixing the appropriate quantity of the mixture containing 4-(4-methyl-4-hydroxyamyl)-Δ³-cyclohexenecarboxaldehyde in the liquid detergent. The detergents all posses a sweet, lilac-lily fragrance, the intensity increasing with greater concentrations of mixture containing 4-(4-methyl-4-hydroxyamyl)-Δ³-cyclohexenecarboxaldehyde.

EXAMPLE XII

PREPARATION OF A COLOGNE AND HANDKERCHIEF PERFUME

A mixture containing 4-(4-methyl-4-hydroxyamyl)-Δ³-cyclohexenecarboxaldehyde prepared according to the process of Example II is incorporated in a cologne at a concentration of 2.5% in 85% aqueous ethanol and into a handkerchief perfume at a concentration of 20% (in 95% aqueous ethanol). A distinct and definite sweet, lilac-lily fragrance is imparted to the cologne and to the handkerchief perfume.

EXAMPLE XIII

PREPARATION OF A COLOGNE AND HANDERCHIEF PERFUME

The composition of Example IX is incorporated in a cologne at a concentration of 2.5% in 85% aqueous ethanol; and into a handkerchief perfume at a concentration of 20% (in 95% aqueous ethanol). The use of the mixture containing 4-(4-methyl-4-hydroxyamyl)-Δ³-cyclohexenecarboxaldehyde in the composition of Example IX affords a distinct and definite strong bouquet aroma with sweet, lilac-lily notes to the handkerchief perfume and cologne.

EXAMPLE XIV

PREPARATION OF SOAP COMPOSITION

One hundred grams of soap chips are mixed with one gram of a mixture containing 4-(4-methyl-4-hydroxyamyl)-Δ³-cyclohexenecarboxaldehyde produced according to Example III, until a substantially homogeneous composition is obtained. The perfumed soap composition manifests an excellent sweet, lilac-lily aroma.

EXAMPLE XV

PREPARATION OF A DETERGENT COMPOSITION

A total of 100 g of a detergent powder is mixed with 0.15 g of the mixture containing 4-(4-methyl-4-hydroxyamyl)-Δ³-cyclohexenecarboxaldehyde prepared according to Example IV until a substantially homogeneous composition is obtained. This composition has an excellent sweet, lilac-lily aroma.

What is claimed is:

1. A process for producing a mixture containing a major proportion of 4-(4-methyl-4-hydroxyamyl)-Δ³-cyclohexenecarboxaldehyde having the structure:

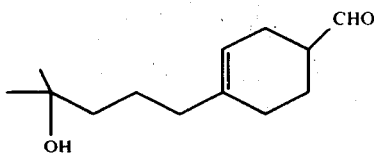

comprising the step of intimately admixing acrolein having the structure:

with myrcenol having the structure:

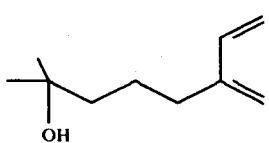

i. In the presence of a catalytic quantity of a ZnCl$_2$ catalyst;
ii. At a temperature in the range of from about −20° C up to about 100° C; and
iii. At a pressure of from about 1 atmosphere up to about 100 atmospheres;

the mole ratio of acrolein reactant:myrcenol reactant being in the range of from about 10:1 up to about 1:10; the weight percent of ZnCl$_2$ catalyst based upon the total weight of acrolein reactant and myrcenol reactant being from about 0.2% up to about 10%.

2. The product produced according to the process of claim 1.

3. A perfume composition comprising a product produced according to a process ccomprising the step of intimately admixing acrolein having the structure:

with myrcenol having the structure:

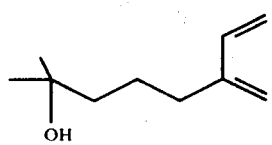

i. In the presence of a catalytic quantity of ZnCl$_2$;
ii. At a temperature in the range of from about −20° C up to about 100° C; and
iii. At a pressure of from about 1 atmosphere up to about 100 atmospheres;

the mole ratio of acrolein reactant:myrcenol reactant being in the range of from about 10:1 up to about 1:10, the weight percent of ZnCl$_2$ catalyst based upon the total weight of acrolein reactant and myrcenol reactant being from about 0.2% up to about 10%, and at least one adjuvant selected from the group consisting of alcohols, other aldehydes, nitriles, esters, cyclic esters and natural essential oils.

4. A cologne comprising a product produced by a process comprising the step of intimately admixing acrolein having the structure:

with myrcenol having the structure:

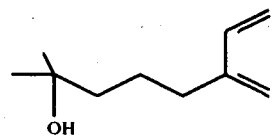

i. In the presence of a catalytic quantity of ZnCl$_2$;
ii. At a temperature in the range of from about −20° C up to about 100° C; and
iii. At a pressure of from about 1 atmosphere up to about 100 atmospheres;

the mole ratio of acrolein reactant:myrcenol reactant being in the range of from about 10:1 up to about 1:10, the weight percent of ZnCl$_2$ catalyst based upon the total weight of acrolein reactant and myrcenol reactant being from about 0.2% up to about 10%, ethanol and water.

* * * * *